US011152664B2

(12) United States Patent
Reykhert

(10) Patent No.: US 11,152,664 B2
(45) Date of Patent: Oct. 19, 2021

(54) COMPACT ELECTRONICS WITH OPTICAL SENSORS

(71) Applicant: ANEXA LABS LLC, Mountain View, CA (US)

(72) Inventor: Alexey Reykhert, Omsk (RU)

(73) Assignee: ANEXA LABS LLC, Mountain View, CA (US)

( * ) Notice: Subject to any disclaimer, the term of this patent is extended or adjusted under 35 U.S.C. 154(b) by 27 days.

(21) Appl. No.: 16/726,580

(22) Filed: Dec. 24, 2019

(65) Prior Publication Data

US 2021/0193977 A1 Jun. 24, 2021

(51) Int. Cl.

| | |
|---|---|
| *H01M 50/216* | (2021.01) |
| *H05K 5/00* | (2006.01) |
| *H05K 9/00* | (2006.01) |
| *H05K 1/14* | (2006.01) |
| *A61B 5/0205* | (2006.01) |
| *G01D 11/24* | (2006.01) |
| *H05K 7/14* | (2006.01) |
| *A61B 5/021* | (2006.01) |
| *A61B 5/145* | (2006.01) |

(Continued)

(52) U.S. Cl.
CPC ....... *H01M 50/216* (2021.01); *A61B 5/02055* (2013.01); *G01D 11/245* (2013.01); *H05K 1/147* (2013.01); *H05K 5/0086* (2013.01); *H05K 7/1427* (2013.01); *H05K 9/0022* (2013.01); *A61B 5/0077* (2013.01); *A61B 5/015* (2013.01); *A61B 5/021* (2013.01); *A61B 5/024* (2013.01); *A61B 5/0536* (2013.01); *A61B 5/1116* (2013.01); *A61B 5/1118* (2013.01); *A61B 5/14532* (2013.01); *A61B 5/14552* (2013.01); *A61B 5/282* (2021.01); *A61B 5/443* (2013.01); *A61B 7/04* (2013.01); *A61B 8/00* (2013.01); *A61B 2562/0219* (2013.01); *A61B 2562/0223* (2013.01); *A61B 2562/164* (2013.01); *A61B 2562/166* (2013.01); *A61B 2562/18* (2013.01); *H01M 2220/30* (2013.01); *H05K 2201/10098* (2013.01); *H05K 2201/10151* (2013.01)

(58) Field of Classification Search
CPC .................................................. A61B 5/02438
See application file for complete search history.

(56) References Cited

U.S. PATENT DOCUMENTS

| | | | |
|---|---|---|---|
| 7,020,508 | B2 | 3/2006 | Stivoric |
| 8,582,546 | B2 | 11/2013 | Rofougaran |

(Continued)

FOREIGN PATENT DOCUMENTS

GB         2147717 A        5/1985

OTHER PUBLICATIONS

International Search Report in International Application No. PCT/US2020/066354, dated Mar. 23, 2021 (2 pages).

*Primary Examiner* — Gary Jackson
*Assistant Examiner* — Anant A Gupta
(74) *Attorney, Agent, or Firm* — Nixon Peabody LLP

(57) ABSTRACT

An electronic device includes a housing, a first printed circuit board (PCB) provided within the housing, a second PCB provided within the housing, and a battery. The second PCB is separate and distinct from the first PCB and is communicatively coupled to the first PCB. The battery is located in a space separating the first PCB and the second PCB. The battery is configured to provide power to the first PCB and the second PCB.

21 Claims, 8 Drawing Sheets

(51) Int. Cl.
  *A61B 5/1455* (2006.01)
  *A61B 5/024* (2006.01)
  *A61B 5/11* (2006.01)
  *A61B 5/00* (2006.01)
  *A61B 5/0536* (2021.01)
  *A61B 5/01* (2006.01)
  *A61B 8/00* (2006.01)
  *A61B 7/04* (2006.01)
  *A61B 5/282* (2021.01)

(56) References Cited

U.S. PATENT DOCUMENTS

| | | | |
|---|---|---|---|
| 9,445,633 B2 | 9/2016 | Tulloch | |
| 10,058,149 B1 | 8/2018 | Wittenberg | |
| 10,257,933 B1* | 4/2019 | Hassemer | H05K 1/147 |
| 10,285,475 B1 | 5/2019 | Tully, Jr. | |
| 10,299,691 B2 | 5/2019 | Hughes | |
| 10,327,520 B1 | 6/2019 | Ely | |
| 2002/0072731 A1* | 6/2002 | Doten | A61B 5/6884 |
| | | | 604/533 |
| 2003/0050010 A1* | 3/2003 | Fallenstein | H04B 5/02 |
| | | | 455/41.1 |
| 2005/0075687 A1 | 4/2005 | Phillips | |
| 2005/0217080 A1 | 10/2005 | Kojoori | |
| 2008/0146871 A1* | 6/2008 | Arneson | A61B 5/073 |
| | | | 600/101 |
| 2009/0177033 A1* | 7/2009 | Hendriks | A61B 1/0019 |
| | | | 600/109 |
| 2009/0235720 A1 | 9/2009 | Smith | |
| 2010/0284436 A1* | 11/2010 | Lane | G01J 5/02 |
| | | | 374/121 |
| 2011/0022411 A1 | 1/2011 | Hjelm | |
| 2011/0098593 A1 | 4/2011 | Low | |
| 2012/0149981 A1* | 6/2012 | Khait | A61B 1/00158 |
| | | | 600/109 |
| 2012/0197144 A1 | 8/2012 | Christ | |
| 2012/0296174 A1* | 11/2012 | McCombie | A61B 5/0404 |
| | | | 600/301 |
| 2013/0302651 A1 | 11/2013 | Kim | |
| 2013/0338448 A1 | 12/2013 | Libbus | |
| 2014/0051946 A1 | 2/2014 | Arne | |
| 2014/0135609 A1* | 5/2014 | Kostenich | A61B 5/0059 |
| | | | 600/407 |
| 2014/0206977 A1 | 6/2014 | Bahney | |
| 2014/0275850 A1 | 9/2014 | Venkatraman | |
| 2015/0212541 A1 | 7/2015 | Lu | |
| 2015/0238094 A1 | 8/2015 | Lai | |
| 2015/0351690 A1 | 12/2015 | Toth | |
| 2016/0037876 A1 | 2/2016 | Perkins | |
| 2016/0120433 A1 | 5/2016 | Hughes | |
| 2016/0192356 A1 | 7/2016 | Lee | |
| 2017/0172413 A1 | 6/2017 | Chakravarthy | |
| 2017/0181510 A1 | 6/2017 | Novak | |
| 2017/0188872 A1 | 7/2017 | Hughes | |
| 2017/0271799 A1 | 9/2017 | Axelowitz | |
| 2017/0296092 A1* | 10/2017 | Jones | A61B 5/6861 |
| 2017/0311812 A1* | 11/2017 | Husheer | G01K 13/20 |
| 2017/0319076 A1* | 11/2017 | McCarthy | A61B 5/7475 |
| 2018/0026393 A1 | 1/2018 | Eid | |
| 2018/0026678 A1 | 1/2018 | Biederman | |
| 2018/0042502 A1 | 2/2018 | Wang | |
| 2018/0214079 A1 | 8/2018 | Banet | |
| 2018/0249767 A1 | 9/2018 | Begriche | |
| 2018/0287115 A1* | 10/2018 | Strong | C23C 18/2086 |
| 2019/0082968 A1* | 3/2019 | Karnik | G06F 3/0482 |
| 2019/0098758 A1 | 3/2019 | Hassemer | |
| 2019/0274597 A1* | 9/2019 | Hoss | A61B 5/14532 |
| 2020/0144777 A1 | 5/2020 | Chahine | |
| 2020/0202083 A1 | 6/2020 | Vartiovaara | |

* cited by examiner

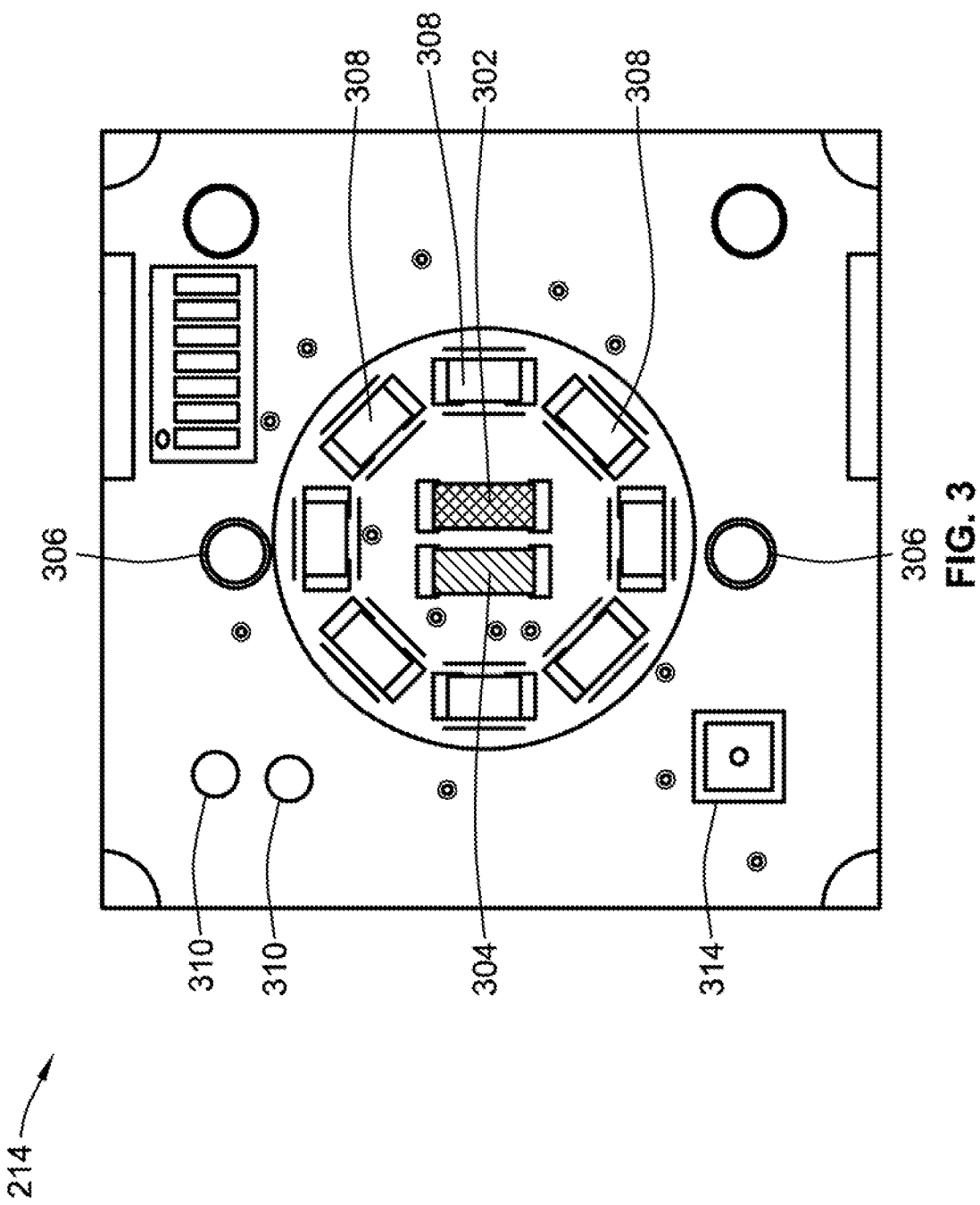

COMPACT ELECTRONICS WITH OPTICAL SENSORS

TECHNICAL FIELD

The present disclosure relates to electronic devices or wearable electronics and more specifically to electronic devices that use a stacked design to integrate electronic components in a compact form factor.

BACKGROUND

Wearable devices are becoming ubiquitous in society. These devices are worn on the human body and are designed to measure one or more parameters. Smartwatches and smart patches are examples of wearable devices that can have multiple sensors and that can pair to a smartphone. Smartwatches can provide health metrics and estimates of the activity level of a human in the form of number of steps the human takes per day, a heart rate of the human, a location of the human, and so on. Smart patches and smartwatches can have similar functionality, but a smart patch can be provided without a display. Unlike smartwatches which can be removed anytime by unbuckling a strap or stretching an elastic band, smart patches typically attach to the user via some adhesive. Also some smart patches (e.g., a chest smart patch) can monitor electrocardiogram (ECG) in real-time continuously compared to a smartwatch which usually requires a user to touch the smartwatch's crown in order to complete a loop and capture ECG data. Furthermore, positioning of smart patches matter so a chest smart patch for capturing ECG signals will provide more accurate results compared to a smartwatch positioned in a user's wrist. Even with the aforementioned differences, smartwatches and smart patches continually benefit from scaling down sizes of electronic components, thus allowing these devices to have more sensors or more powerful processors for additional functionality. Besides scaling down sizes of electronic components, other design options, as provided in the present disclosure, can be explored for packing more electronic components into these devices.

SUMMARY

Some implementations of the present disclosure provide an electronic device. The electronic device includes: a housing, a first printed circuit board (PCB) provided within the housing, a second PCB provided within the housing, and a battery. The second PCB is separate and distinct from the first PCB and is communicatively coupled to the first PCB. The battery is located in a space separating the first PCB and the second PCB. The battery is configured to provide power to the first PCB and the second PCB.

Some implementations of the present disclosure provide an electronic device. The electronic device includes a housing, N printed circuit boards (PCBs) provided within the housing, and at least N−1 battery layers, where N>1. Each of the N PCBs is a separate and distinct PCB and is communicatively coupled to other ones of the N PCBs. Each of the at least N−1 battery layers includes one or more batteries. The at least N−1 battery layers are configured to electromagnetically shield adjacent PCBs within the N PCBs and provide power to the N PCBs.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 3 illustrates a sensor board for the electronic device of FIG. 1A, according to some implementations of the present disclosure;

Figure 1A:
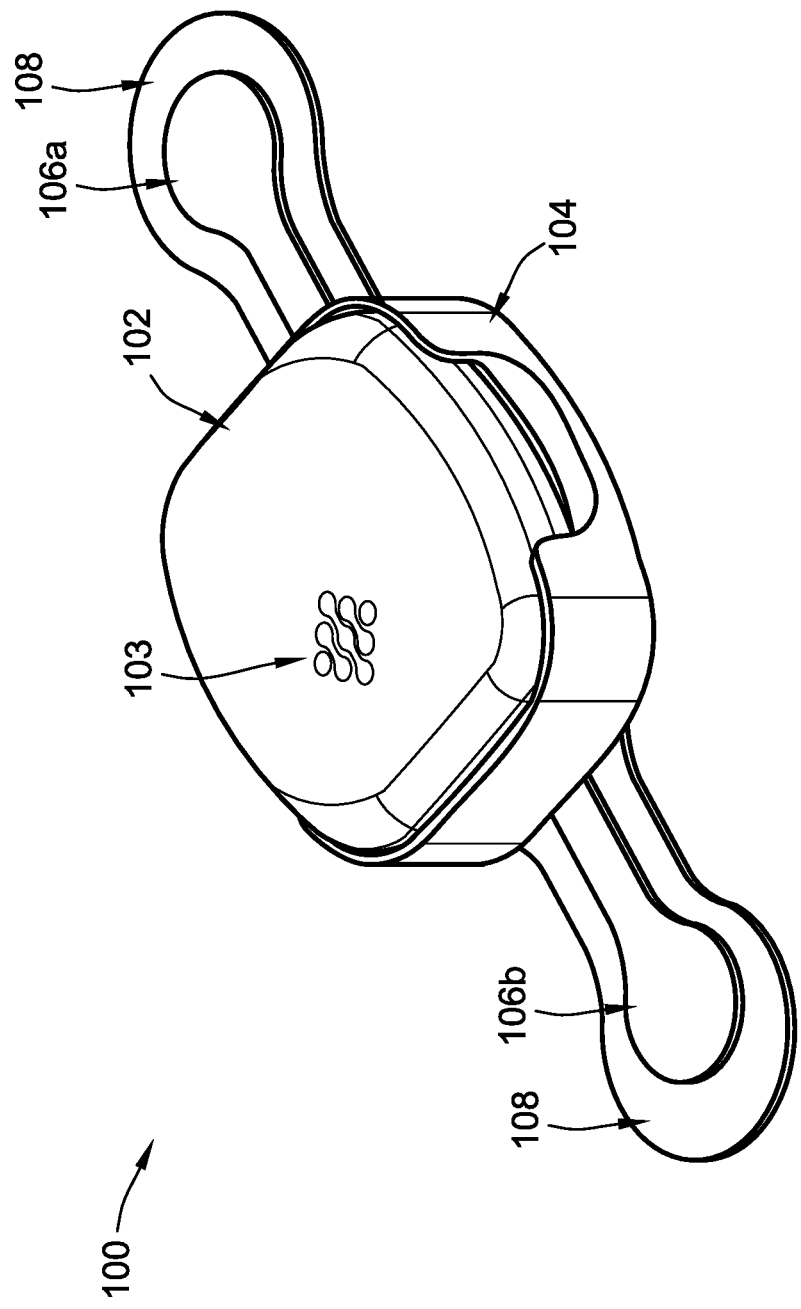
FIG. 1A illustrates an electronic device for monitoring health metrics of a user, according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

Embodiments of the present disclosure provide a stacked design of an electronic device for compactly arranging components within a housing of the electronic device. The stacked design separates components of the electronic device and arranges the components in such a way that space within the housing of the electronic device is used more efficiently. Space is an important design variable because as electronic devices continue to shrink in size, space becomes a more valuable resource. For example, smartphones and smartwatches can perform some similar functions. Form factor of a smartphone can allow for a relatively larger-sized printed circuit board (PCB) compared to a PCB of a smartwatch. Since more components can be placed on a relatively larger-sized PCB compared to a relatively smaller-sized PCB, smartphones generally have more components on their PCBs and generally have better performance specifications compared to smartwatches. Stacked designs according to embodiments of the present disclosure can allow more components to be included in a smartwatch, thus providing an avenue to increase performance specifications.

Stacked designs can be used in various electronic devices where efficiently utilizing space within a housing is important. Examples of these electronic devices include smartphones, smartwatches, wristbands, smart patches, implantable medical devices, smart stethoscopes, smart bandages, smart rings, fitness trackers, posture trainer devices, smart glasses with PCBs inside frames, devices with built-in sensors, smart shoe insoles or inserts, head wearable devices, smart bracelets, smart jewelry, wireless earbuds, wireless headphones with in-ear sensors, portable medical devices for imaging, digital streaming dongles (e.g., High-Definition Multimedia Interface streaming dongles), smart speakers, toys, tablets, e-book readers, flat screen televisions, etc. An example of an electronic device with a stacked design will be described in connection with FIGS. 1A-4B, and a more generalized description of a stacked design is described in connection with FIG. 5.

Referring to FIG. 1A, an electronic device 100 for monitoring health metrics of a user is illustrated according to some implementations of the present disclosure. The electronic device 100 is a smart patch with removable parts. The electronic device 100 includes a body 102, a base 104, one or more electrodes 106a, 106b . . . , and an adhesive 108 for holding the electrodes 106 in place. The body 102 includes electronic components encased in a housing. The body 102 is removably coupled to the base 104. The base 104 can receive the body 102, allowing the body 102 to pressure fit snugly in the base 104. The body 102 can include a logo 103. The logo 103 can include one or more LED lights. The logo 103 can include a frosted and/or opaque material like plastic, crystal glass, etc., which is backlit with LED lights to give a translucent appearance.

Figure 1B:
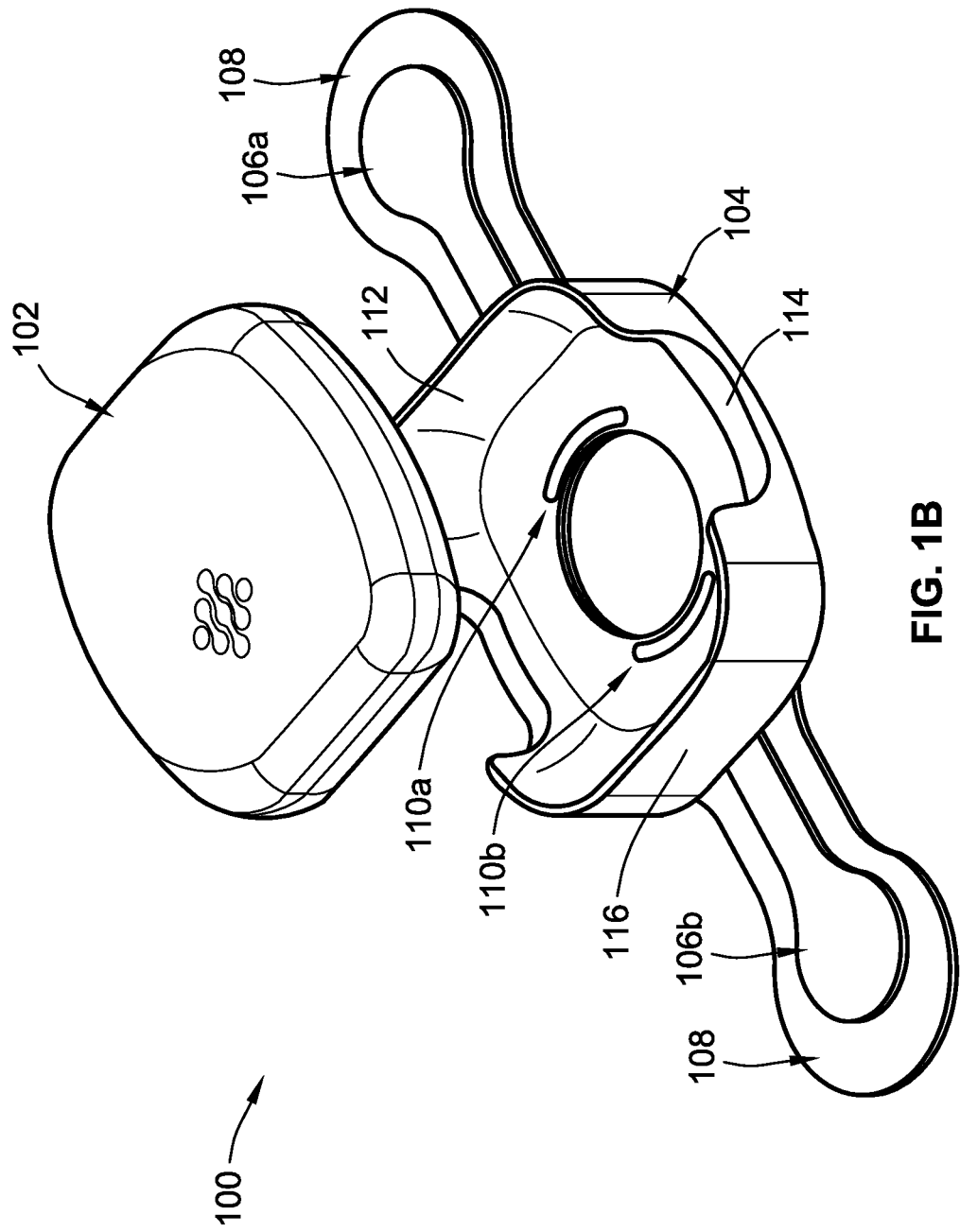
FIG. 1B illustrates a body of the electronic device of FIG. 1A separated from a base of the electronic device, according to some implementations of the present disclosure.

FIG. 1B illustrates the body 102 of the electronic device 100 separated from the base 104 of the electronic device 100. The base 104 is shown to have an inner surface 112 with a concave-in contour for receiving the body 102. The base 104 can include one or more cutouts or receded sidewalls 114 to facilitate removing or decoupling the body 102 from the base 104. The base 104 is configured to hold the body 102 in place when the body 102 is coupled to the base 104. The base 104 can hold the body 102 in place via a friction force created between the inner surface 112 and the housing of the body 102 when the body 102 is coupled to the base 104 as depicted in FIG. 1A. The housing of the body 102 can pressure fit with the base 104, holding the body 102 in place. With minimal modification, the body 102 can be secured to the base 104 using other methods.

In some implementations, the body 102 and the base 104 can include a latch for securing the body 102 to the base 104. For example, an outer surface 116 of the base 104 can include a recess (or catch) for receiving a lever or an arm attached to the body 102. In another example, the body 102 can include one or more protruding portions, and the inner surface 112 can include one or more recesses for catching the protruding portions of the body 102. These methods of securing the body 102 to the base 104 are non-limiting and are merely provided as examples.

The base 104 is further configured to provide an opening such that an electrode end 110a of the electrode 106a and an electrode end 110b of electrode 106b is accessible via the inner surface 112 of the base 104. Two electrodes 106a and 106b are shown as examples in FIGS. 1A-1B, but more than two electrodes can be coupled to the base 104. The electrodes 106 can be positioned on the adhesive 108. The adhesive 108 can secure the electrodes 106 in place on the skin of the user. In some implementations, the adhesive 108 can also secure the base 104 to the electrodes 106.

In some implementations, the electrodes 106 provided in the adhesive 108 have a male or female gender to them. Such that, complementary gendered electrodes are provided on a bottom of the base 104. That way, the adhesive 108 holds the male and/or female gendered electrodes to the skin of the user, and when the base 104 is coupled to the electrodes, the complementary gendered electrodes interface with the male and/or female gendered electrodes. The complementary gendered electrodes can snap onto the male and/or female gendered electrodes, securing the base 104 to the adhesive 108. Examples of gendered electrodes include adhesive button electrodes, electrocardiogram (ECG) electrodes, or any other adhesive electrode with a snap fastener.

Although the base 104 is included in the electronic device 100 as depicted in FIGS. 1A and 1B, in some implementations, the base 104 is not included. For example, the adhesive 108 with the electrodes 106 can be configured to mechanically hold the body 102 in place on the skin of the user while also electrically connecting the electrodes 106 to electronic components in the body 102. Methods of holding the body 102 in place can include using complementary electrodes as previously discussed in connection to securing the base 104 to the adhesive 108 and the electrodes 106. Gendered electrodes can be provided as the electrodes 106 and complementary gendered electrodes can be provided on the body 102. Such that, the complementary gendered electrodes on the body 102 snap onto the gendered electrodes provided on the adhesive layer.

Figure 2A:
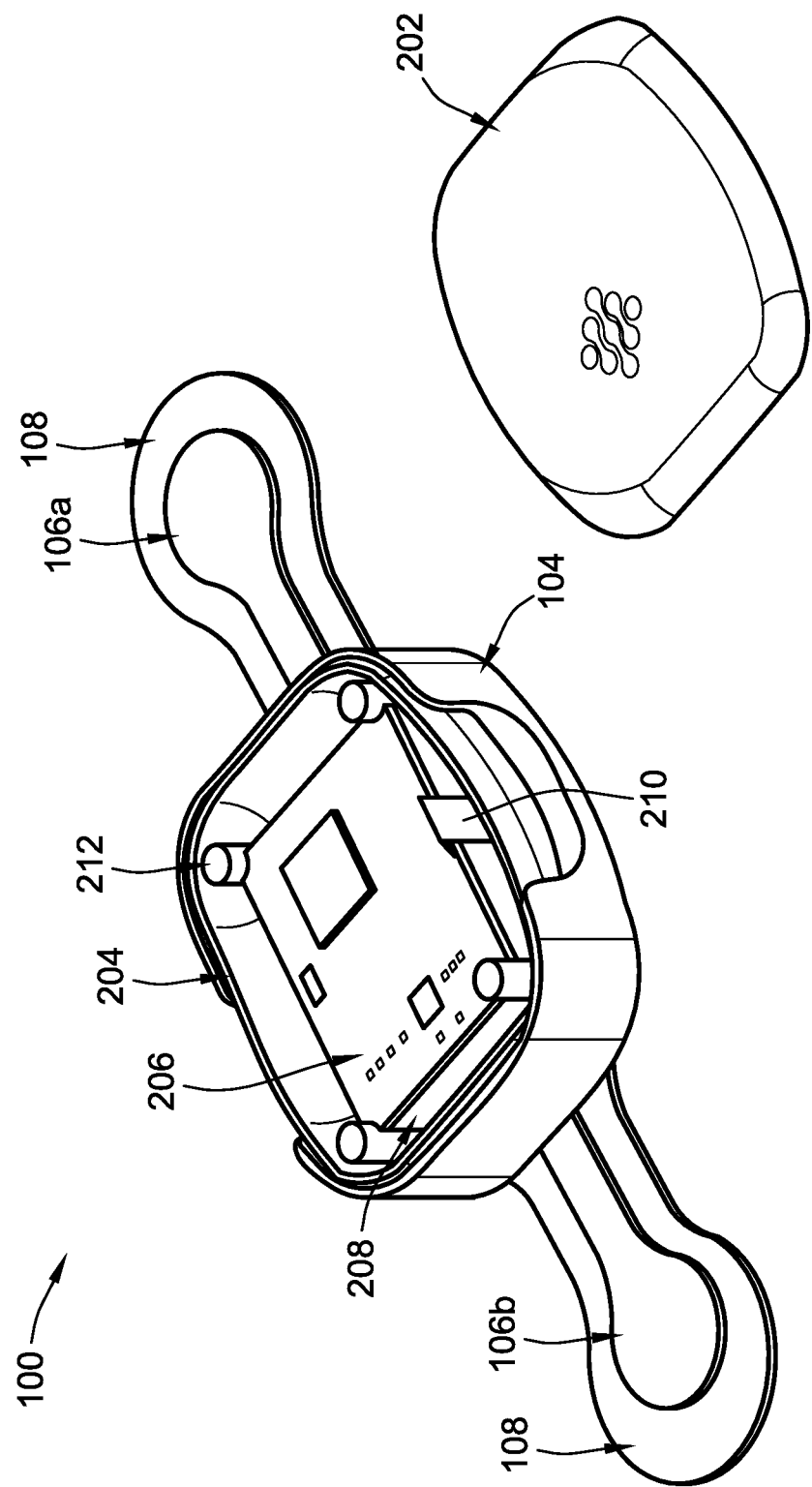
FIG. 2A illustrates an interior of the body of the electronic device of FIG. 1A, according to some implementations of the present disclosure.

Referring to FIG. 2A, an interior of the body 102 of the electronic device 100 of FIG. 1A is illustrated according to some implementations of the present disclosure. The housing of the body 102 is shown to include two portions, a top housing portion 202 and a bottom housing portion 204. The top housing portion 202 is configured to serve as a covering while the bottom housing portion 204 is configured to hold electronic components of the body 102. The bottom housing portion 204 can include a main printed circuit board (PCB) 206 and a mechanical holder 208 for preventing the main PCB 206 from moving. The bottom housing portion 204 can also include a flexible PCB connector 210 for connecting the main PCB 206 to other electronic components within the body 102. The bottom housing portion 204 can further include one or more bottom guides 212 for keeping the electronic components in the body 102 from moving laterally within the body 102. The one or more bottom guides 212 can match one or more top guides (not shown) for aligning the top housing portion 202 with the bottom housing portion 204. Corners of the rectangular shape of the main PCB 206 are shown to have a contour that substantially matches a circular cross-sectional shape of the one or more bottom guides 212. The shape of the main PCB 206 can be engineered to match a shape of the housing in which the main PCB 206 sits.

Figure 2B:
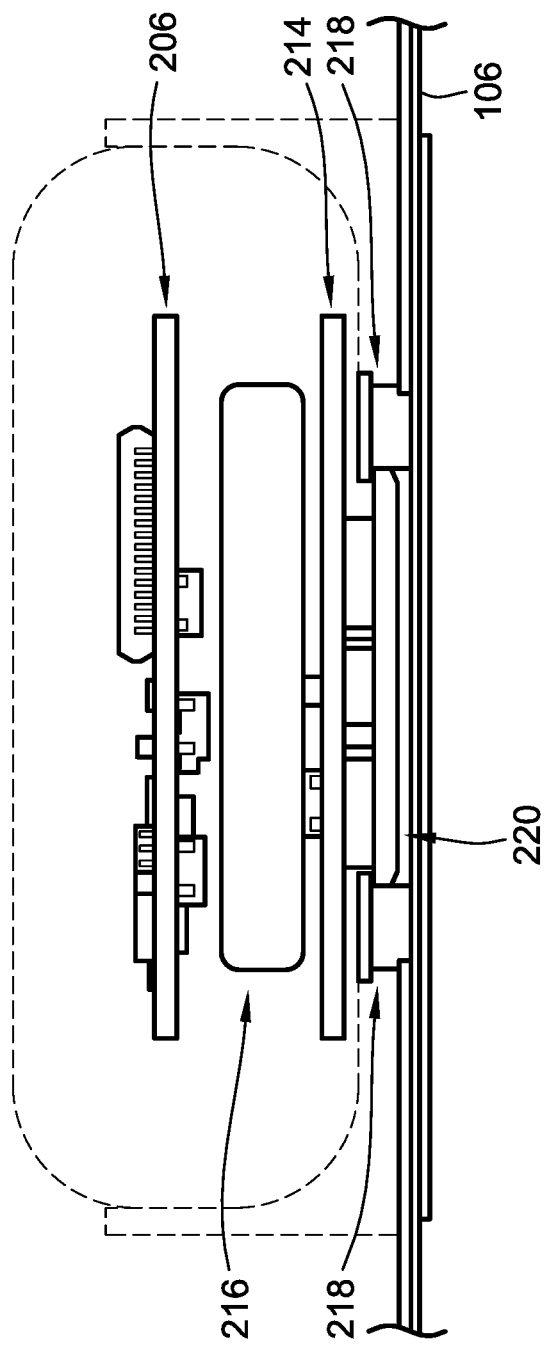
FIG. 2B illustrates an arrangement of the interior of FIG. 2A, according to some implementations of the present disclosure.

FIG. 2B illustrates an arrangement of the interior of FIG. 2A when the body 102 is coupled to the base 104, according to some implementations of the present disclosure. In some implementations, multiple printed circuit boards (PCBs) can be provided in the body 102 according to a form factor of the body 102. The multiple PCBs allow for vertically stacking the PCBs to conserve space when compared to using one PCB. The main PCB 206 can include one or more processors, memory, filters, etc. The one or more processors can include multicore processors, graphics processing units (GPUs), artificial intelligence (AI) accelerator chips, neural processors, etc. A sensor PCB 214 can be provided that includes sensors, analog to digital converters, digital to analog converters, memory, etc. A battery 216 can be provided to power the multiple PCBs. An example of the battery is a 3.7V, 500 mAh lithium polymer (LiPo) battery. The battery 216 can be a regular battery or a flexible, thin-film battery. A vertical stacking of the sensor PCB 214, the battery 216, and the main PCB 206 as shown in FIG. 2B is an example of a stacked design, according to some implementations of the present disclosure. The main PCB 206, the battery 216, and the sensor PCB 214 can be centered around a vertical axis (as shown in FIG. 2B) such that none of these components are staggered.

At the bottom of the body 102, a housing window material 220 can be provided to protect electrical and other sensitive components of the electronic device 100 from outside contaminants (e.g., water, humidity, etc.) as well as provide a clear path for optical sensors, imaging sensors, thermal imaging sensors, laser sensors or other sensors performing non-contact measurements on the skin of the user. The imaging sensors can provide an image of the skin of the user, and the thermal imaging sensors can provide a thermal image of the skin of the user. Metal connectors 218 are provided to facilitate connection of the electrodes 106 to the sensor PCB 214. The main PCB 206 and/or the sensor PCB 214 can be rigid PCBs or flexible PCBs.

In some implementations, visual indicators can be used for signaling. For example, visual indicators can signal that the electronic device 100 is capturing data, battery level of the battery 216 is low, that there is an issue to troubleshoot, etc. For example, the logo 103 can light up in green color during data capture. The logo 103 can turn red if the battery is low or if there if some issue to troubleshoot. Although color is used as an example, the logo 103 can incorporate a sequence of flashes and brightness to distinguish between the different signaling.

FIG. 3 illustrates a bottom side of the sensor board 214 of the electronic device 100 depicted in FIG. 1A, according to some implementations of the present disclosure. The sensor board 214 can include one or more emitters, for example, one or more light emitting diodes (LEDs). The one or more LEDs can be different LEDs, for example, the sensor board 214 provides a red LED 304 and an infrared LED 302. The red LED 304 can emit light in a wavelength range between 600 nm and 750 nm, for example, at about 650 nm wavelength. The infrared LED 302 can emit light in a wavelength range between 850 nm and 1000 nm, for example, at about 940 nm wavelength. The sensor board 214 can include one or more photodetectors, for example, photodiodes 308. The photodiodes 308 can measure both red and infrared light. The photodiodes 308 can be arranged around a center as shown in FIG. 3. The photodiodes 308 can be arranged around the red LED 304 and the infrared LED 302. The combination of the one or more emitters and the one or more photodetectors can be used as an optical array measurement system. Arranging the photodiodes 308 around the center can introduce redundancy that minimizes effects of noise attributed to the skin of the user moving, a heart of the user moving, and so on. In an example, arranging optical sensor arrays around a center can improve robustness of oxygen level sensor values obtained via the photodetectors and the emitters. Although the photodiodes 308 are arranged around the center, other photodiode arrangements are within the scope of the present disclosure.

The sensor board 214 can include one or more charging pads 310. The one or more charging pads 310 are configured to conduct charge for charging a battery connected to the sensor board 214, for example, the battery 216 of FIG. 2B. The charging pads 310 can be made of copper.

The sensor board 214 can include one or more electrode pads 306 for facilitating sending and receiving signals from electrodes, for example, the electrodes 106 of FIG. 1A. Although two electrode pads 306 are depicted in FIG. 3, the number of electrode pads 306 can vary based on a number of the electrodes 106.

The sensor board 214 can include a temperature sensor 314. The temperature sensor 314 can be a contactless temperature sensor configured to obtain temperature of the user without contacting a body part of the user. In some implementations, the sensor board 214 can connect to the electrodes 106 which contact the skin of the user, and the electrodes 106 can conduct the temperature from the skin to the temperature sensor. The sensor board 214 can include one or more connecting pads for connecting the sensor board 214 to the electrodes 106 contacting the skin of the user, such that heat data can be transferred from the skin via the electrodes 106 and the conducting pads to the temperature sensor. The temperature sensor can then determine temperature from the heat data. The conducting pads can be copper pads.

Non-limiting examples of sensors that can be provided in the electronic device 100 include temperature sensor, a pulse oximeter, an accelerometer, a gyroscope, a magnetometer, a radar sensor, an impedance spectroscopy measurement unit, optical array sensors, a photoplethysmogram (PPG) sensor, an ECG sensor, a microphone array, a camera, a thermal imaging camera, one or more lasers, ultrasonic vibration sensors, an inertial measurement unit (IMU), or any combination thereof. The IMU includes the accelerometer, the gyroscope, and the magnetometer. The IMU can generate data for indoor navigation, step counting, walking speed, running speed, sleep monitoring, distance moved by the user, and motion of the user. Sensors of the electronic device 100 can generate physiological data including a glucose level of the user, a blood pressure of the user, a blood oxygen saturation (SpO2) of the user, a heart rate of the user, an ECG waveform of the user, a level of skin moisture of the user, a humidity level, a temperature of the user, an activity level of the user, a body position of the user, a body orientation of the user, or any combination thereof.

The electronic device 100 can include one or more network interfaces for communicating with other electronic or computer devices. The one or more network interfaces can include wired or wireless interfaces. For example, the one or more network interfaces can support Wi-Fi, Bluetooth, Bluetooth Low Energy (BLE), cellular networks like 3G, 4G, 5G, etc. The electronic device 100 can support subscriber identity module (SIM) and/or embedded SIM for use with any of the wired and/or wireless interfaces.

The one or more network interfaces can also include a global positioning system (GPS) receiver for generating location data of the electronic device 100. In some implementations, the one or more network interfaces can use wireless technologies supported to allow a microprocessor of the electronic device 100 to run an indoor positioning system. For example, the network interface with Wi-Fi support can be used for Wi-Fi based positioning systems. In some implementations, the network interface can include an ultra-wide band (UWB) chip for precise indoor location positioning for monitoring movement in hospitals, nursing homes, patient homes, offices, etc. In some implementations, the network interface can receive a semantic location of the electronic device 100 based on the generated location data. For example, based on GPS receiver location data, the electronic device 100 can be determined to be at the Golden State Bridge (semantic location).

In some implementations, the network interface includes NFC or other wireless technologies for automatic setup and wireless pairing of the electronic device 100 with another electronic or computer device (e.g., a smartphone/other device that exchanges settings via NFC). NFC can also be used to automatically transmit health metrics from the electronic device 100.

Figure 4A:
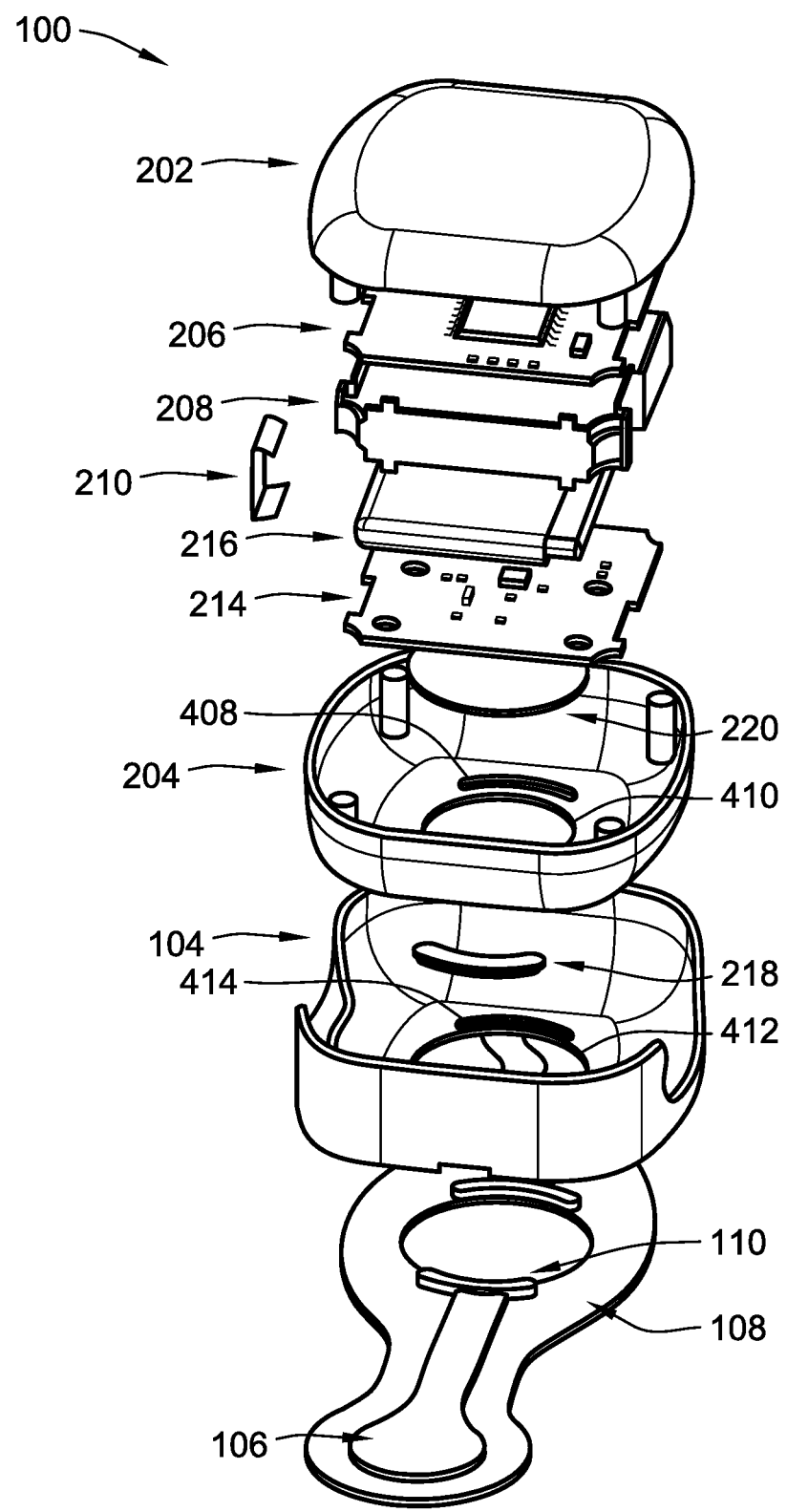
FIG. 4A illustrates components in the electronic device of FIG. 1A, according to some implementations of the present disclosure.

FIG. 4A illustrates components in the electronic device 100 of FIG. 1A, according to some implementations of the present disclosure. The electronic device 100 includes the top housing portion 202 and the bottom housing portion 204. Enclosed within the top housing portion 202 and the bottom housing portion 204 are the main PCB 206, the holder 208, the flexible PCB connector 210, the battery 216, and the sensor board 214. The bottom housing portion 204 can include one or more housing openings, for example, the housing openings 408, and/or one or more housing windows, for example, the housing window 410.

The housing window material 220 is engineered to cover the housing window 410. The housing window material 220 protects the electronic components of the body 102 from outside elements, for example, liquid, dust, and/or other particles. The housing window material 220 prevents these outside elements from entering the body 102 via the housing window 410. The housing window material 220 can be a translucent material including plastic, sapphire crystals, mineral crystals, plexiglass, hesalite crystals, glass, etc. Although the housing window material 220 and the housing window 410 are shown to have a circular shape, other shapes can be used. For example, the housing window material 220 and the housing window 410 can be shaped as a square, a rectangle, a polygon, an oval, etc.

The housing window 410 is provided as an example, but more than one housing window can be provided. For example, the electronic device 100 can have as many housing windows as a total number of photodetectors and light emitters. In another example, the electronic device 100 can have as many housing windows as a total number of line of sight sensors, for example optical sensors, imaging sensors, thermal imaging sensors, laser sensors, etc. Each respective photodetector and/or light emitters can have a dedicated housing window or can share a housing window with another photodetector and/or light emitter. For example, two light emitters can share a housing window, two photodetectors share another housing window, three photodetectors share yet another housing window, and one photodetector has its dedicated housing window. A housing window material can be provided for all housing windows of the bottom housing portion 204.

The housing openings 408, different from the housing window 410, are configured to allow electrical connections to the sensor board 214 from components outside the body 102. The housing openings 408 can take the shape of one or more metal connectors 218 that interface with the housing opening 408. The one or more metal connectors 218 are designed to plug the housing openings 408 such that the housing openings 408 are sealed when the body 102 is coupled to the base 104 as depicted in FIG. 1A. In some implementations, when in the configuration as depicted in FIG. 1A, the electronic device 100 is waterproof.

In some implementations, the base 104 includes a base window 412. The base window 412 is shown as circular, but other shapes can be envisioned. Unlike the housing window 410, the base window 412 is not filled with any material and is just an opening that substantially matches the housing window 410 on the body 102. When the body 102 is coupled to the base 104, the housing window 410 and the base window 412 are aligned such that sensors on the sensor board 214 can send light from the sensor board 214 to the base window 412 via the housing window 410, and the sensors on the sensor board 214 can receive light from the base window 412 via the housing window 410.

In some implementations, the base 104 includes one or more electrode openings 414 for receiving the electrodes 106. The electrode openings 414 can have a shape that substantially matches the one or more metal connectors 218. The electrode openings 414 can also have a shape that substantially matches the electrode ends 110 of the electrodes 106.

In some implementations, one or more metal connectors 218 are configured to receive the electrode ends 110. The electrode ends 110 protrude from the one or more electrode openings 414, and the one or more metal connectors 218 snap onto the electrode ends 110. When snapped onto the electrode ends 110, the one or more metal connectors 218 have an electrical connection to the electrodes 106. When snapped onto the electrode ends 110, the one or more metal connectors 218 hold the base 104 in place between the electrodes 106 and the one or more metal connectors 218.

In some implementations, the one or more metal connectors 218 are configured to be inserted in the one or more electrode openings 414 in the base 104 (from the inner surface of the base 104). When inserted, the one or more metal connectors 218 make contact with the electrode ends 110 inserted from the outer surface of the base 104. The one or more metal connectors 218 and the electrode ends 110 are designed to fit snugly into the one or more electrode openings 414.

In some implementations, the adhesive 108 not only supports and secures the electrodes 106 on the user's skin, but a top layer of the adhesive 108 contacting the base 104 can removably attach to the outer surface of the base 104. The base 104 can be designed to plug in and out the body 102 and send ECG electrical signals to the sensor board 214 of the body 102. The base 104 can be designed to replace the adhesive electrodes 106 easily if the adhesive electrode 106 is broken or old.

Figure 4B:
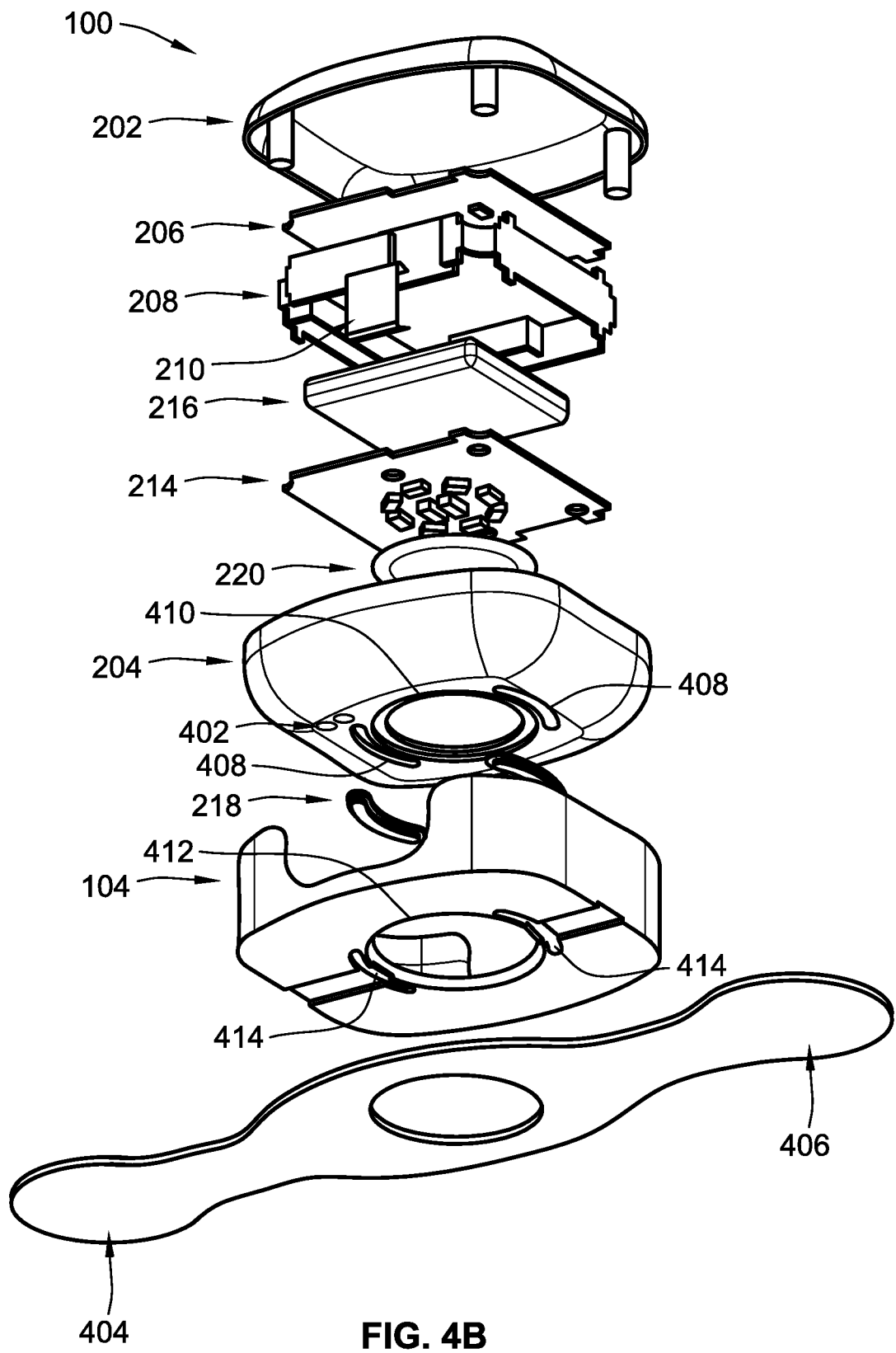
FIG. 4B illustrates the components in FIG. 4A from another perspective.

FIG. 4B illustrates the components in FIG. 4A from another perspective. In FIG. 4B, a two electrode configuration can be used for ECG measurements. For example, electrode sitting at position 404 on the adhesive 108 can represent an LA terminal for ECG measurements, and electrode sitting at position 406 on the adhesive 108 can represent the RA terminal. Also in FIG. 4B, one or more charging ports 402 are provided for interfacing the body 102 to a charging station (not shown).

Figure 5:
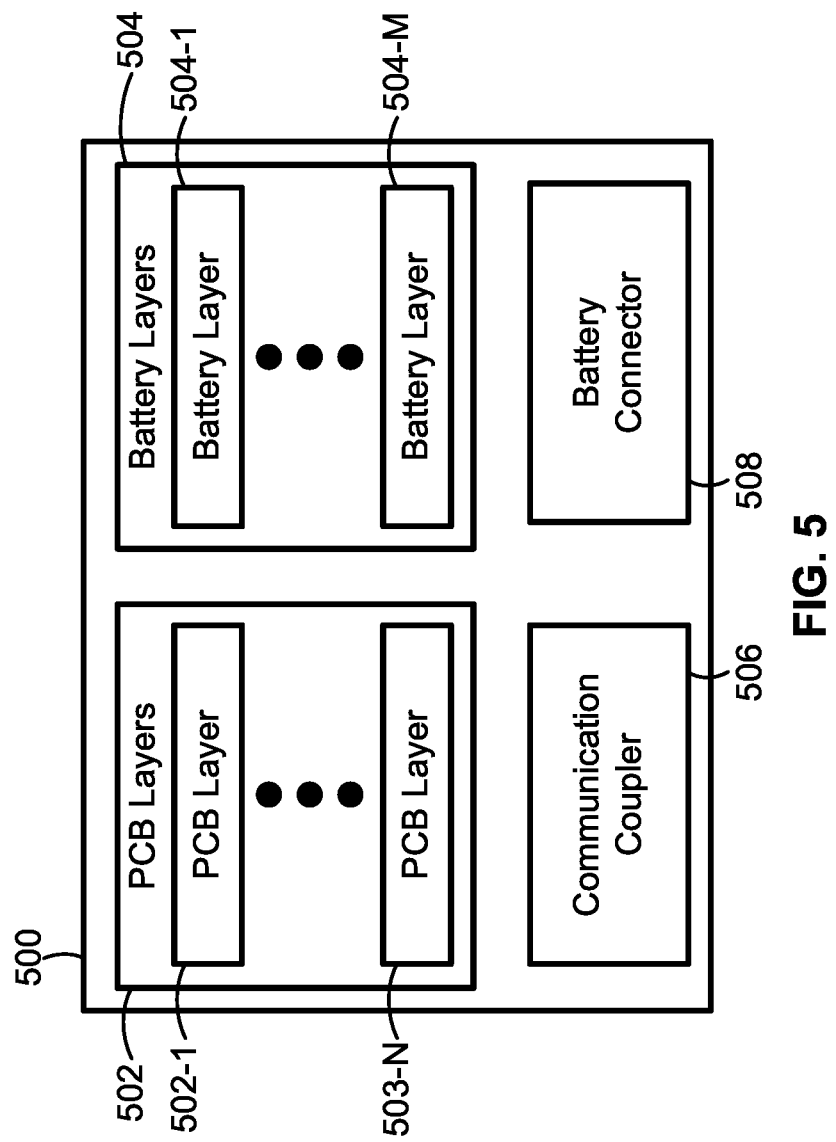
FIG. 5 is a block diagram of an electronic device with a stacked design, according to some implementations of the present disclosure.

FIG. 5 is a block diagram of an electronic device 500 with a stacked design, according to some implementations of the present disclosure. The electronic device 500 includes two or more PCB layers 502 and one or more battery layers 504. The electronic device 500 also includes a communication coupler 506 and a battery connector 508. The communication coupler 506 enables the PCB layers 502 to transmit electrical signals between each other. The battery connector 508 facilitates a power connection from the battery layers 504 to the PCB layers 502. To simplify discussion, the singular form will be used for all components identified in FIG. 5 when appropriate, but the use of the singular does not limit the discussion to only one of each such component.

The electronic device 100 of FIG. 1A can be described in terms of the generalized stacked structure provided in FIG. 5. The two or more PCB layers 502 can include N PCB layers described as PCB layer 502-1, ..., PCB layer 502-N. Referring to FIG. 4A, the electronic device 100 includes two PCB layers (i.e., N=2), and the two PCB layers are the main PCB 206 and the sensor PCB 214. The one or more battery layers 504 can include M battery layers described as battery layer 504-1, . . . , battery layer 504-M. Referring to FIG. 4A, the electronic device 100 includes one battery layer (i.e., M=1) with the battery 216.

The communication coupler 506 facilitates signal transmission between two or more PCBs in the PCB layers 502. Referring to FIG. 4A, the flexible PCB connector 210 connects the main PCB 206 to the sensor PCB 214 and allows electronic signals to be passed between the main PCB 206 and the sensor PCB 214. The flexible PCB connector 210 is an example of the communication coupler 506. Other examples of the communication coupler 506 include devices or components that facilitate wireless coupling, for example, infrared communication devices, radio communication, optical wavelength communication, etc.

The battery connector 508 facilitates power transmission from the battery layers 504 to the PCB layers 502. Referring to FIG. 4A, the battery 216 can have a physical connection to the main PCB 206, the sensor PCB 214, or both. The physical connection to any of the PCBs is an example of the battery connector 508. In some implementations, if the battery 216 is only connected to one of the main PCB 206 or the sensor PCB 214, then the flexible PCB connector 210 can include power buses or power rails that share power from the battery 216 to the PCB not connected to the battery 216. As such, the communication coupler 506 can be used to jump power from one PCB layer to another PCB layer.

Referring to FIG. 4A, the battery 216 can be sandwiched between the main PCB 206 and the sensor PCB 214. The battery 216 being placed between the main PCB 206 and the sensor PCB 214 can serve as a shield to block electromagnetic radiation (EMR) between the main PCB 206 and the sensor PCB 214. Also shown FIG. 4A, longitudinal axes of each of the main PCB 206, the sensor PCB 214, and the battery 216 are all parallel to each other in the stacked design. The centers of the main PCB 206, the sensor PCB 214, and the battery 216 can be stacked vertically such that a circle with a fixed radius contains each of the main PCB 206, the sensor PCB 214, and the battery 216 and none of the PCBs or the battery are staggered.

FIG. 4A shows the electronic device 100 has one battery (i.e., the battery 216) serving as a battery layer. In some implementations, the battery layers 504 can have different configurations. For example, the battery layer 504-1 can include two batteries connected in series configuration or in parallel configuration. In other examples, the battery layer 504-1 can include three batteries, four batteries, etc. Some of the batteries in the battery layer 504-1 can be connected in series while some of the batteries can be connected in parallel. Examples of batteries that can be arranged in one layer include lithium coin or cell batteries.

In some implementations with two or more battery layers, the two or more battery layers can be connected to one other using a flexible connector, multi-wire connectors or single wire connections. For example, the battery layer 504-1 can be connected to the battery layer 504-2. From a layer connectivity perspective, the battery layer 504-1 can be connected to the battery layer 504-2 in a parallel configuration or in a series configuration. Battery layers within the battery layers 504 can have different voltage, current, or power capacities. For example, the battery layer 504-1 can provide 4V between its terminals, the battery layer 504-2 can provide 2V, and the battery layer 504-3 can provide 2V. In connecting the different layers, the battery layer 504-2 and the battery layer 504-3 can be connected in series to provide 4V. The series combination of the battery layer 504-2 and the battery layer 504-3 can then be connected in parallel to the battery layer 504-1.

In some implementations, the number of battery layers M is one less than the number of PCB layers N (i.e., M is equal to N−1). In some implementations, each of the M battery layers 504 is sandwiched between two of the PCB layers 502. In some implementations, M and N are decoupled from each other such that M is greater than or equal to one and N is greater than or equal to two. That way, there can be one battery layer 504-1 providing power to three or more PCB layers 502.

Although described above that the battery layers 504 can be configured in series and parallel connections such that the battery layer 504-2 is serially connected to the battery layer 504-3, other configurations are possible.

Furthermore, one or more PCB boards and/or one or more batteries can be rigid and/or flexible. For example, one or more PCB boards are rigid, or one or more batteries are flexible. In another example, all PCBs and batteries are rigid. In yet another example, all PCBs and batteries are flexible.

Embodiments of the present disclosure provide a stacked design for an electronic device. The stacked design incorporates vertical stacking of one or more batteries and two or more printed circuit boards. The vertical stacking allows for space within a housing of the electronic device to be better utilized. The stacked design can use components (e.g., PCBs and batteries) that contour with inside walls of the housing of the electronic device. Along with the components having a shape that substantially matches inside walls of the housing of the electronic device, the components can be designed to be flexible such that they can further bend to utilize empty volume within the housing of the electronic device. The stacked design allows more components to be packed into a relatively smaller form factor of the electronic device to improve performance specifications of the electronic device.

While the present disclosure has been described with reference to one or more particular implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. An electronic device, comprising:
a housing including at least two portions mechanically interfacing with each other to form an enclosure, each of the at least two portions bounding the enclosure, wherein a bottom portion of the at least two portions includes a distinct housing window that is sealed with a translucent material such that light originating within the enclosure can pass through the housing window;
a first printed circuit board (PCB) provided within the enclosure defined by the housing;
a second PCB provided within the enclosure defined by the housing, the second PCB being separate and distinct from the first PCB and being communicatively coupled to the first PCB;
optical array sensors provided on the second PCB that generate measurements via the sealed housing window;
a battery located in a space separating the first PCB and the second PCB, the battery configured to provide power to the first PCB and the second PCB; and
a mechanical holder, separate from the housing and provided within the enclosure, the mechanical holder configured to secure the battery such that the battery is sandwiched between the second PCB and the first PCB.

2. The electronic device of claim 1, wherein the battery is positioned to substantially block electromagnetic radiation (EMR) between the first PCB and the second PCB.

3. The electronic device of claim 1, wherein the battery, the first PCB, and the second PCB have a longitudinal axis that are all parallel to each other.

4. The electronic device of claim 3, wherein a cross-sectional center of the first PCB, a cross-sectional center of the second PCB, and a cross-sectional center of the battery are within a circle of a fixed radius, such that the first PCB, the second PCB, and the battery overlap and are not staggered.

5. The electronic device of claim 1, wherein the electronic device is one selected from the group consisting of: a smartphone, a watch, a wristband, a smart patch, implantable medical devices, a smart stethoscope, a smart bandage, a smart ring, a fitness tracker, a posture trainer device, smart glasses with PCBs inside frames, a device with built-in sensors, a smart shoe insole or insert, a head wearable device, a smart bracelet, smart jewelry, wireless earbuds, wireless headphones with in-ear sensors, and a portable medical device for imaging.

6. The electronic device of claim 5, wherein the second PCB is positioned to be closer to the skin of a user of the electronic device compared to the first PCB.

7. The electronic device of claim 1, wherein the first PCB includes a microcontroller unit, a network interface, a storage device, or any combination thereof.

8. The electronic device of claim 1, further comprising:
a flexible PCB connector configured to electrically connect the first PCB to the second PCB, wherein the flexible PCB facilitates communications between the first PCB and the second PCB, power sharing between the first PCB and the second PCB, or both.

9. The electronic device of claim 1, wherein the first PCB and the second PCB are communicatively coupled via wireless interfaces on each of the first PCB and the second PCB.

10. The electronic device of claim 1, wherein the housing is waterproof.

11. The electronic device of claim 1, wherein the second PCB in cooperation with the first PCB is configured to measure a glucose level of a user, a blood pressure of the user, a blood oxygen level of the user, a heart rate of the user, a level of skin moisture of the user, a temperature of the user, an activity level of the user, a body position of the user, an image of a skin of the user, a thermal image of the skin of the user, an electrocardiogram waveform, or any combination thereof.

12. The electronic device of claim 1, wherein the second PCB includes one or more sensors, the one or more sensors including a temperature sensor, a pulse oximeter, an accelerometer, an impedance spectroscopy measurement unit, cameras, thermal imaging sensors, infrared sensors, microphones, ultrasound sensors, radar sensors, a gyroscope, a magnetometer, an impedance measurement unit, an inertial measurement unit, an electrocardiogram sensor, or any combination thereof.

13. The electronic device of claim 12, wherein the one or more sensors are positioned on the second PCB such that the one or more sensors face away from the battery.

14. The electronic device of claim 12, wherein the temperature sensor interprets data from one or more electrodes positioned outside of the housing, the one or more electrodes conducting heat data to the temperature sensor via one or more copper pads.

15. An electronic device, comprising:
a housing including at least two portions mechanically interfacing with each other to form an enclosure, each of the at least two portions bounding the enclosure, wherein a bottom portion of the at least two portions includes a distinct housing window that is sealed with a translucent material such that light originating within the enclosure can pass through the housing window;
a plurality of printed circuit boards (PCBs) provided within the housing, each of the plurality of PCBs being separate and distinct PCBs and being communicatively coupled to each other;
optical array sensors, provided on one of the plurality of PCBs, that generate measurements via the sealed housing window;
at least one battery layer provided within the housing, each of the at least one battery layer including one or more batteries, wherein the at least one battery layer is configured to electromagnetically shield adjacent PCBs within the plurality of PCBs and provide power to the plurality of PCBs; and
a mechanical holder, separate from the housing and provided within the enclosure, the mechanical holder configured to sandwich the at least one battery layer between multiple PCBs of the plurality of PCBs within the enclosure.

16. The electronic device of claim 15, wherein the at least one battery layer are two or more battery layers connected in (i) a series configuration, (ii) a parallel configuration, or (iii) a combination of both (i) and (ii).

17. The electronic device of claim 15, wherein for a respective one of the at least one battery layer with two or more batteries, the two or more batteries are connected in (i) a series configuration, (ii) a parallel configuration, or (iii) a combination of both (i) and (ii).

18. The electronic device of claim 15, further comprising:
at least one flexible PCB connector configured to form electrical connections between at least two PCBs in the plurality of PCBs.

19. The electronic device of claim 15, wherein one or more of the plurality of PCBs is rigid, one or more of the plurality of PCBs is flexible, one or more of the at least one battery layer is rigid, one or more of the at least one battery layer is flexible, or any combination thereof.

20. The electronic device of claim 1, wherein the optical array sensors are positioned proximate to the housing window of the bottom portion such that a distance between the optical array sensors and the housing window is less than a distance between the optical array sensors and a top portion of the at least two portions of the housing, and wherein the first PCB is positioned between the top portion of the housing and the optical array sensors.

21. The electronic device of claim 15, wherein the optical array sensors are positioned proximate to the housing window of the bottom portion such that a distance between the optical array sensors and the housing window is less than a distance between the optical array sensors and a top portion of the at least two portions of the housing, and wherein another one of the plurality of PCBs is positioned between the top portion of the housing and the optical array sensors.

* * * * *